United States Patent [19]

Takahashi

[11] 4,302,422
[45] Nov. 24, 1981

[54] SYSTEM AND PROCESS FOR TOTAL GASEOUS NONMETHANE ORGANIC ANALYSIS

[75] Inventor: Yoshihiro Takahashi, San Jose, Calif.

[73] Assignee: Envirotech Corporation, Menlo Park, Calif.

[21] Appl. No.: 135,595

[22] Filed: Mar. 31, 1980

[51] Int. Cl.³ .............................................. G01N 31/06
[52] U.S. Cl. ........................................ 422/88; 422/94; 23/232 R; 73/23
[58] Field of Search .......... 23/230 M, 230 PC, 232 R, 23/232 C, 232 E; 422/88, 89, 54, 93, 94, 98; 73/23, 23.1; 55/179, 180, 270

[56] References Cited

U.S. PATENT DOCUMENTS

| | | | |
|---|---|---|---|
| 3,111,835 | 11/1963 | Jenkins | 23/232 C |
| 3,585,002 | 6/1971 | Boys | 23/232 C |
| 3,859,417 | 1/1975 | Telle | 423/244 |
| 3,935,294 | 1/1976 | Telle | 423/224 |
| 4,003,257 | 1/1977 | Fletcher et al. | 23/232 C |
| 4,042,332 | 8/1977 | Saitoh et al. | 23/232 C |
| 4,102,648 | 7/1978 | Hartmann et al. | 23/232 E |

OTHER PUBLICATIONS

Federal Register, vol. 44, No. 195, pp. 57,792–57,822.
"Dohrmann DC-50 Series–Laboratory Total Organic Carbon Analyzers" Envirotech Brochure 1977.
Heftman, Erich, *Chromatography*, Van Nostrand Reinhold Co., N.Y., 1975, pp. 916–919, 883–887.
Baker, W. J. et al., "Control Engineering", vol. 8, pp. 77–81 (1961).

Primary Examiner—William F. Smith
Attorney, Agent, or Firm—Robert E. Krebs; Thomas J. McNaughton

[57] ABSTRACT

A system and process for determining the concentration of nonmethane organic chemicals in a gaseous sample includes a separation system to receive the gaseous sample. In the separation system nonmethane organic chemicals including ethylene and ethane are reversibly retained on a packing material while methane and inert gases pass through the separation system and are vented. Thereafter a carrier gas is directed through the separation system, the nonmethane organic chemicals are released into the carrier gas, and the carrier gas containing the organic chemicals is conveyed to an analyzer for analysis of the organic chemicals.

4 Claims, 2 Drawing Figures

SYSTEM AND PROCESS FOR TOTAL GASEOUS NONMETHANE ORGANIC ANALYSIS

BACKGROUND OF THE INVENTION

1. Field of the Invention

The present invention is for a system for the chemical analysis of gases which are potential atmospheric pollutants.

2. State of the Art

The determination of the concentration of organic chemicals in a gaseous sample is important in the control of air pollution. Many industries generate large quantities of gaseous organic compounds which are discharged into the atmospheres. While in the atmosphere the organic substances often undergo complex chemical interactions to produce chemicals collectively known as photochemical smog. The exact nature of all the chemical interactions involved in the production of photochemical smog is presently unknown. However, it is believed that methane, $CH_4$, is not involved in the production of photochemical smog.

In order to reduce the production of photochemical smog, regulatory agencies such as the U.S. Environmental Protection Agency place limitations upon the amounts of organic chemcials which may be emitted into the atmosphere by industries. Such regulation requires monitoring of the organic emissions from the industries. Since it is believed that most, if not all, organic chemicals, with the important exception of methane, are involved in the production of photochemical smog, the analysis of organic emissions for organic chemicals other than methane is important. The chemicals which should be analyzed for are collectively known as total gaseous nonmethane organic chemicals (TGNMO). However, there is presently no analyzer for TGNMO which is satisfactory in terms of being simple and easy to use and giving accurate results.

There are known methods and systems for analyzing samples of gases to determine the concentration of volatile organic compounds therein. For example, U.S. Pat. No. 4,003,257 teaches a system for analyzing volatile organic compounds by gas chromatography. According to the patent, a gaseous sample is passed through a sample trap which contains an absorbent material such as a polymer of 2,6-diphenyl-p-phenylene oxide (PPPO) sold commercially under the registered trademark Tenax GC. As the sample flows through the sample trap, volatile organic compounds are absorbed on the absorbent while other compounds pass through and are vented to the atmosphere. After this step of absorption has been completed, the sample trap is coupled to a gas chromatograph, and a carrier gas is transferred through the sample trap while the trap is heated. Thereby the absorbed volatile organics are desorbed into the carrier gas and the carrier gas, along with the volatile organics, is transferred to the gas chromatograph. In the gas chromatograph, the various organic compounds are separated and analyzed to determine the concentration of each compound.

This patented system includes a complex means for separating by gas chromatography the various constituents of the sample. Furthermore, the patented system is believed not to analyze for certain important organic chemicals including ethane and ethene, for example.

SUMMARY AND OBJECTS OF THE INVENTION

The present invention is directed to an improved system and process for analyzing for TGNMO, total gaseous nonmethane organic chemicals.

The presently preferred embodiment includes a sample separation system to receive a gaseous sample and to separate therefrom the TGNMO chemicals while permitting methane and certain inorganic chemicals to pass through and be vented to the atmosphere. The nonmethane organic chemicals are reained in the separation system, and after completion of the separation step, the separation system is coupled to a system for analyzing for the amount of organic chemicals. Then a stream of inert carrier gas is passed through the separation system while the separation system is heated so that the organic chemicals are released into the carrier gas. The carrier gas carries the organic chemicals to the analyzer system wherein the concentration of organic chemicals is determined.

The separation system according to the preferred embodiment includes three columns packed with material, and the columns are interconnected so that the sample flows into the first column, and thence into the second and thereafter the third columns in sequence and is thereafter vented into the atmosphere. The first column is packed with porous polymers such as Tenax GC and Chromosorb 101 and is maintained at a temperature of about 60° C. during the separation step. The column reversibly retains such chemicals as methanol, acetone, benzene and water. However, the column does not retain such chemicals as carbon dioxide, ethylene, ethane, and methane. The second column is packed with lithium hydroxide and is maintained at about 25° C. during separation step. The lithium hydroxide chemically reacts with carbon dioxide so that the carbon dioxide is removed from the gas stream. The third column is filled with graphitized carbon and maintained at about 100° C. The graphitized carbon retains ethane and ethylene and certain other organic compounds while permitting methane, as well as other chemicals such as nitrogen and oxygen, to pass through to be vented to the atmosphere.

After the sample has been completely passed through the separation system, the flow of the carrier gas through the separation system is stopped and the system is coupled to a reducing catalyst and a flame ionization detector. Then carrier gas is passed through the three columns in sequence, and the temperature of the first column is raised to 120° C. to drive off the absorbed organic chemicals. The organic chemicals are carried by the carrier gas through the reducing catalyst which converts all the organic chemicals in the sample to methane. The methane is then quantitatively measured in the flame ionization detector. Thus, it can be seen that the total amount of organic chemicals, other than methane, in the original sample is quickly and easily determined by the flame ionization detector.

It should be particularly noted that not only the organic chemicals which are absorbed in the first column but also the ethane and ethylene are measured by the flame ionization detector. Thus, it can be appreciated that substantially all of the organic chemicals, other than methane, present in the original sample are measured by the flame ionization detector.

It can be seen that the present embodiment accomplishes the objectives of the present invention which include providing a simple and effective system for measuring total gaseous nonmethane organic compounds.

A further object of the present invention is to provide a system for measuring TGNMO without the necessity of utilizing an expensive gas chromatograph to separate the organic chemicals from one another and the necessity for the time-consuming determination of the quantity of each particular chemical.

Further objects and advantages of the present invention can be readily ascertained by reference to the following description and drawings, which are offered by way of example and not in limitation of the invention, the scope of which is defined by the claims and by equivalents to the structure, materials and acts set forth therein.

DESCRIPTION OF PRESENTLY PREFERRED EMBODIMENTS

Figure 1:
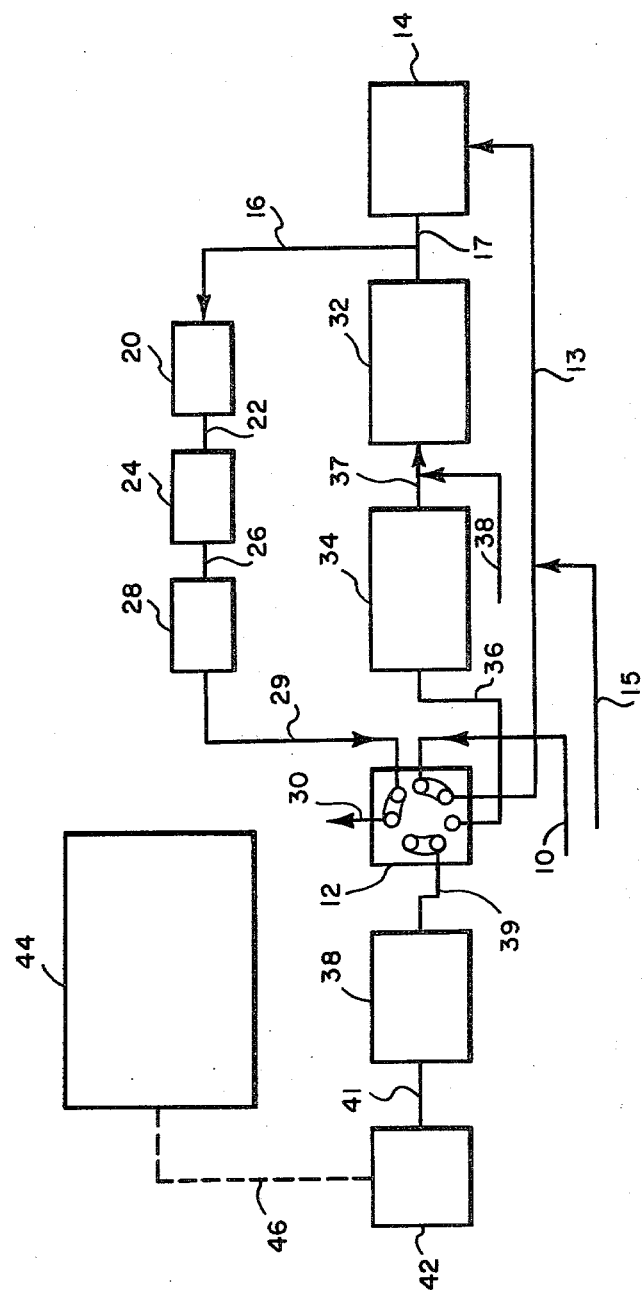
FIG. 1 is a schematic diagram of the presently preferred embodiment illustrating its operation during the separation stage.
Figure 2:
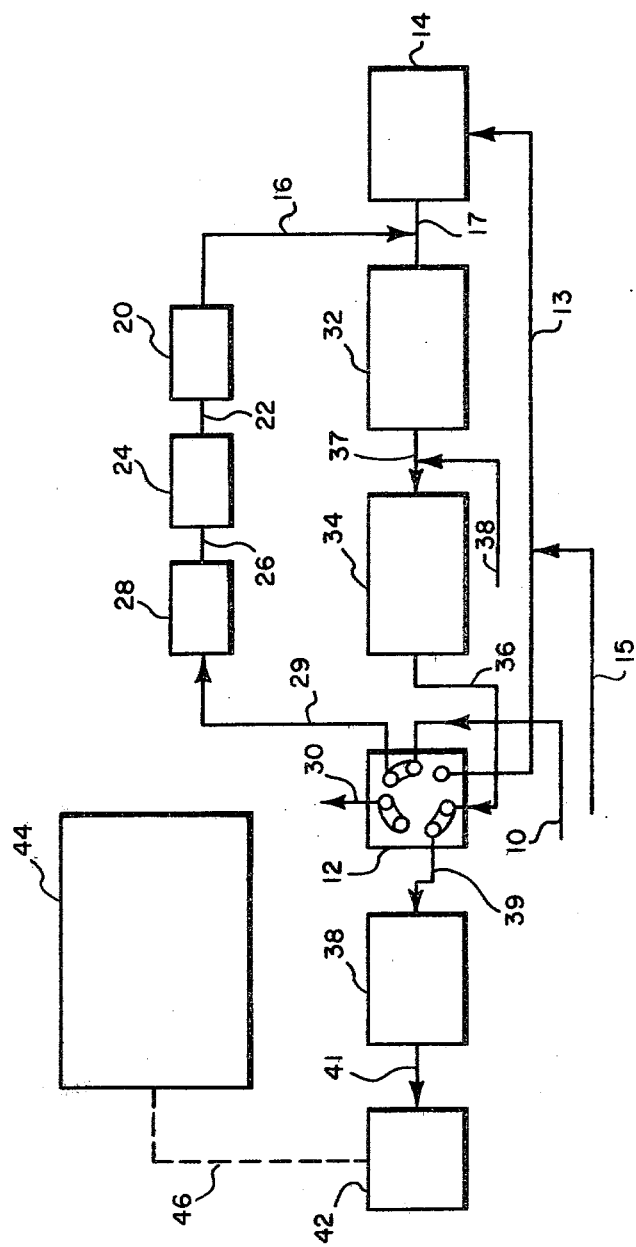
FIG. 2 is a schematic diagram of the embodiment shown in FIG. 1 illustrating the operation during the analysis stage.

The presently preferred embodiment illustrated in FIG. 1 includes a source of carrier gas 10, such as helium which is connected to a valve 12. The valve 12 is coupled to a line 13 and also to other parts of the system as discussed below. The valve 12 is adjustable to one of two positions to permit interconnection of certain parts of the system as shown in FIGS. 1 and 2. When the valve is in the position shown in FIG. 1, it interconnects line 10 with line 13. The line 13 is connected to injection valve 14, which is constructed to receive the sample to be analyzed from a source not shown. A line 15, coupled to a source of purge gas, is connected to line 13. A line 17 is coupled to receive gas from the injection valve 14, and a line 16 is coupled to the line 17 to conduct the mixture of carrier gas and sample to a first column 20.

The first column 20 is a packed column filled with a porous polymer which is capable of reversibly retaining certain organic chemicals. In particular, the first column must be capable of sorbing polar organic chemicals and high and medium weight organics including methanol, acetone, and benzene, while permitting methane to pass through. The first column 20 should also have the characteristic that when heated, the sorbed organic chemicals are released from the packing material.

One packing material which exhibits the required characteristics is a combination of a porous polymer based on 2,6-diphenyl-p-phenylene oxide (PPPO) sold commercially under the trademark Tenax GC and a cross-linked styrene and di-vinyl benzene co-polymer sold commercially under the trademark Chromosorb 101. I have found that Tenax GC reversibly retains high molecular weight organic compounds, but cannot effectively retain medium molecular weight organic compounds. However, Chromosorb 101 reversibly retains medium molecular weight organic compounds but irreversibly retains high molecular weight organic compounds. High and medium molecular weight organic chemicals are those having a carbon number greater than three. Column 20 is packed with Tenax GC near the end coupled to line 16 and with Chromosorb 101 in the end coupled to line 22. Thus, the advantages of both compounds are realized, so that organic compounds having a carbon number greater than three are reversibly retained. Column 20 retains the required organic compounds at about 60° C., and when the column temperature is raised to about 120° C., the organic chemicals are rapidly released from the packing.

A heating means for heating the column 20 to selected temperatures is coupled thereto; however, the heating means is not shown.

A second column 24 is coupled by line 22 to receive the gases from the first column 20. The column 24 is similar to column 20; however, column 24 is preferably packed with a chemical which irreversibly retains carbon dioxide while permitting other compounds to pass through unaffected. By way of example, and without limitation, lithium hydroxide, LiOH, sodium hydroxide NaOH or calcium oxide, CaO as well as certain other basic compounds are appropriate for use in packing the second column 24. The second column 24 is in contact with the atmosphere so that the temperature thereof is about 25° C.

A line 26 is coupled to the column 24 to convey gases therefrom to a third column 28. The third column 28 is a conventional packed column which reversibly retains organic compounds having the formula $C_nH_m$ where n is greater than one and equal to or less than 3 and m is greater than or equal to n and equal to or less than $2n+2$. (An alternative way of stating the values of n and m are that n is greater than one and less than 4 and m is greater than $n-1$ and less than $2n+3$). Compounds which are reversibly retained on the third column 28 include ethane, $C_2H_6$, ethylene, $C_2H_4$, and acetylene, $C_2H_2$. By way of example, and without limitation, graphitized carbon is a suitable packing material for column 28. Graphitized carbon is sold under the trademark Carbosieve B. A heating means, not shown, is coupled to the third column 28.

The third column 28 is coupled to the valve 12 by line 29. When the valve 12 is in the position shown in FIG. 1, the gas from line 29 is vented to the atmosphere via line 30.

After the sample has been passed through the system, the valve is oriented as shown in FIG. 2. According to FIG. 2, it can be seen that the valve 12 blocks the inlet end of line 13 while connecting line 10 with line 29. Thus, the direction of flow of the carrier gas through the columns is reversed. The line 16 is coupled to line 17, which in turn is coupled to a pyrolysis furnace 32 to heat the gases and convert high molecular weight compounds to compounds of lower molecular weight. The furnace 32 is connected to reduction zone 34 by line 37 and a line 38 is coupled to line 37 to convey a carrier gas from a source, not shown, into the line 37. The reduction zone contains a reducing catalyst, which for example, and without limitation, can be nickel or rhodium supported on alumina. The reducing zone 34 is coupled by line 36 to the valve 12 which connects line 36 to humidifier 38 by line 39. The humidifier 38 is coupled to a flame ionization detector 42 by line 41. The detector 42 is electrically connected to an integrator 44 by cable 46.

The system comprising the pyrolysis zone 32, the reduction zone 34 and the flame ionization detector 42, can be a total organic carbon analyzer manufactured by the Dohrmann Division of Envirotech Corporation under the trademark DC-50 Total Organic Carbon Analyzer. The system comprising the columns 20, 24 and 28 is referred to herein as the separation system.

In operation of the system illustrated in FIG. 1, a gaseous sample is introduced into the injection valve 14 to be mixed therein with carrier gas flowing through line 13. The mixture of gaseous sample and carrier gas is conveyed by line 16 to the first column 20. It should be appreciated that during this separation phase of the operation, the first column 20 is maintained at a temperature of about 60° C.; the second column 24 is maintained at a temperature of about 25° C.; and the third column 28 is maintained at a temperature of about 100° C.

The gas is introduced by line 16 into the first column 20 to flow therethrough to column 24 and thereafter to the third column 28. In the first column 20, organic chemicals are reversibly retained on the packing material. For example, and without limitation, methanol, $CH_3OH$; acetone, $CH_3COCH_3$; benzene, $C_6H_6$ and water are reversibly retained on the first column. However, methane, $CH_4$ and certain other chemicals are not retained on the first column 20. That part of the sample which was not retained in the first column 20 is conveyed to the second column 24 wherein carbon dioxide, $CO_2$, is retained. The remaining gases are transferred to the third column 28 wherein organic chemicals having the general formula $C_nH_m$ where n is greater than one and equal to or less than 3 and m is greater than or equal to n and equal to or less than $2n+2$ are retained, while methane, $CH_4$, carbon monoxide, oxygen and nitrogen are permitted to pass through and be vented to the atmosphere via line 30. It should be appreciated that the second column 24 is important in that if carbon dioxide were present in the gas admitted to the third column 28, the column would adsorb the carbon dioxide and later release it during the analysis step.

In practice it has been found that the separation phase should be accomplished in about one minute. During this time the chemicals which are retained in the first and third columns 20 and 28 are not stationary therein, but slowly move from the inlet end of the column toward the outlet end. Thus, if the carrier gas passes through the columns for less than about one minute substantially all of the organic chemicals are retained in the columns; however if a longer time were used, organics would be flushed from the columns.

After the separation phase has been completed and all the sample gas has been transferred through the three columns, the valve 12 is reoriented so that the system is in the configuration shown in FIG. 2. At this time the temperature of the first column 20 is increased to about 120° C. so that the organic chemicals sorbed thereon are rapidly released from the packing material. The stream of carrier gas is introduced through line 29 into the third column 28 and thence through the second and then the first columns and into the line 17. While the carrier gas is passing through the columns, the organic chemicals are desorbed from the packing materials and carried with the carrier gas into line 16. The carrier gas and organic chemicals are carried by a line 16 to the pyrolysis furnace 32 and thence to be mixed with hydrogen gas introduced by line 30, and the mixture is introduced into the reducing zone 34. In the reducing zone 34 all organic materials are converted to methane, and thereafter the methane is tranferred to the flame ionization detector 42. The flame ionization detector 48 continuously measures the concentration of methane in the sample passing therethrough. The conventional integration device 44 determines the total amount of methane which is passed through the detector 42.

It should be understood that conversion of the organic chemicals to methane is important because if the flame ionization detector 42 received the unconverted organic compounds, it would not provide an accurate measurement of the number of molecules of carbon received. In contrast, the quantity of methane measured by the flame ionization detector 42 is representative of the total quantity of TGNMO in the original sample.

I claim:

1. An analyzer for determining the concentration of non-methane organic chemicals in a gaseous sample comprising:

means for analyzing a gaseous sample;

first column means for initially receiving the gaseous sample to be analyzed and to reversibly retain at least any methanol, acetone and benzene while permitting at least methane and carbon dioxide to pass through;

second column means downstream of the first column means for thereafter receiving the treated gaseous sample from said first column means and to irreversibly retain any carbon dioxide while permitting at least methane to pass through;

third column means coupled downstream of the second column means for thereafter receiving the treated gaseous sample from said second column means and to reversibly retain at least any ethylene and ethane while permitting at least methane to pass through;

flushing means coupled to said column means to flush the reversibly retained chemicals from said first, second and third column means; and means for coupling said analyzing means to receive the chemicals flushed by said flushing means so as to enable the analyzing means to determine the concentration of organic chemicals in the received chemicals.

2. The analyzer of claim 1 wherein said first column means includes a first packing material comprised of 2,6-diphenyl-p-phnylene oxide and a second packing material comprised of a cross-linked styrene and divinyl benzene copolymer, whereby the fist material reversibly retains high molecular weight organic compounds and said second material reversibly retains medium molecualr weight organic compounds, said first packing material being arranged upstream of the second packing means.

3. The analyzer according to either claim 1 or claim 2 wherein said second column means includes a packing comprised of lithium hydroxide.

4. The analyzer according to claim 3 wherein said third column means include packing material comprised of graphitized carbon.

* * * * *